(12) United States Patent
Hull, Jr.

(10) Patent No.: US 9,320,538 B2
(45) Date of Patent: Apr. 26, 2016

(54) HANDHELD, PERSONAL SKIN CARE SYSTEMS WITH DETACHABLE SKIN CARE ELEMENTS

(71) Applicant: JOHNSON & JOHNSON CONSUMER INC., Skillman, NJ (US)

(72) Inventor: Raymond J. Hull, Jr., Hampton, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

(21) Appl. No.: 14/244,956

(22) Filed: Apr. 4, 2014

(65) Prior Publication Data

US 2014/0249548 A1 Sep. 4, 2014

Related U.S. Application Data

(60) Continuation of application No. 13/713,178, filed on Dec. 13, 2012, now Pat. No. 8,709,019, which is a division of application No. 12/770,994, filed on Apr. 30, 2010, now Pat. No. 8,500,754.

(51) Int. Cl.
*A61B 17/3205* (2006.01)
*A45D 34/04* (2006.01)
(Continued)

(52) U.S. Cl.
CPC ............. *A61B 17/3205* (2013.01); *A45D 34/04* (2013.01); *A61B 17/50* (2013.01);
(Continued)

(58) Field of Classification Search
CPC .................. A61B 17/3205; A61B 2017/00761; A61H 23/0254

USPC ................ 606/131; 601/69–73; 132/73.5, 75, 132/73.6, 75.8, 76.4; 451/353, 359
See application file for complete search history.

(56) References Cited

U.S. PATENT DOCUMENTS

| 5,704,902 A | * | 1/1998 | Vandenbelt et al. ............ 601/72 |
| 6,010,268 A | | 1/2000 | Sereg et al. |

(Continued)

FOREIGN PATENT DOCUMENTS

| EP | 1943999 A | 7/2008 |
| EP | 2020191 A | 2/2009 |

(Continued)

OTHER PUBLICATIONS

U.S. Appl. No. 14/601,697, filed Jan. 21, 2015, Batchvarova et al.
(Continued)

*Primary Examiner* — Thomas McEvoy

(57) ABSTRACT

A skin care element holder is designed for use with a handheld body having a receptacle. The skin care element holder includes a substantially circular plate having a diameter between about 20 and about 60 mm. The substantially circular plate has a first surface arranged and configured for coupling to the skin care element; a second surface, opposite the first surface; and an outer peripheral edge. The second surface of the substantially circular plate has at least one spacer leg; a plurality of engagement arms; and at least one key. Each of the at least one spacer leg, engagement arms and key extend from the second surface in a direction away from the first surface. The at least one spacer leg supports the plate in the receptacle. At least one of said engagement arms includes a snap-fit projection for engagement with a recess in the receptacle. The key is arranged and configured to fit into a notch in the receptacle. Handheld skin care systems incorporating the skin care holder are also described.

2 Claims, 5 Drawing Sheets

(51) Int. Cl.
*A61B 17/54* (2006.01)
*A61B 17/50* (2006.01)
*A61B 17/00* (2006.01)
*A61B 17/32* (2006.01)

(52) U.S. Cl.
CPC ........ *A61B 17/54* (2013.01); *A45D 2200/1054* (2013.01); *A45D 2200/207* (2013.01); *A61B 2017/00398* (2013.01); *A61B 2017/00473* (2013.01); *A61B 2017/00477* (2013.01); *A61B 2017/00734* (2013.01); *A61B 2017/00761* (2013.01); *A61B 2017/320004* (2013.01); *A61B 2017/320012* (2013.01)

(56) References Cited

U.S. PATENT DOCUMENTS

| | | | |
|---|---|---|---|
| 6,139,553 | A | 10/2000 | Dotan |
| 6,652,888 | B2 | 11/2003 | Rhoades |
| 7,306,569 | B2 | 12/2007 | LaJoie et al. |
| 8,308,702 | B2 | 11/2012 | Batchvarova et al. |
| 8,500,754 | B2 | 8/2013 | Hull, Jr. |
| 8,709,019 | B2 | 4/2014 | Hull, Jr. |
| 2001/0018061 | A1 | 8/2001 | Rhoades |
| 2001/0046506 | A1 | 11/2001 | Rhoades |
| 2003/0125754 | A1 | 7/2003 | Davis et al. |
| 2003/0165550 | A1 | 9/2003 | Rhoades |
| 2004/0236291 | A1 | 11/2004 | Zelickson et al. |
| 2005/0222525 | A1 | 10/2005 | Muchisky |
| 2006/0058714 | A1 | 3/2006 | Rhoades |
| 2007/0010828 | A1 | 1/2007 | Eknoian et al. |
| 2010/0168626 | A1 | 7/2010 | Gubernick et al. |
| 2010/0198119 | A1 | 8/2010 | Gubernick et al. |
| 2011/0258796 | A1 | 10/2011 | Batchvarova et al. |
| 2011/0262645 | A1 | 10/2011 | Batchvarova et al. |

FOREIGN PATENT DOCUMENTS

| | | |
|---|---|---|
| EP | 2022420 A | 2/2009 |
| WO | WO 2007/015729 A | 2/2007 |

OTHER PUBLICATIONS

European Search Report dated Jul. 25, 2011, for corresponding EP application 11164134.6.

* cited by examiner

HANDHELD, PERSONAL SKIN CARE SYSTEMS WITH DETACHABLE SKIN CARE ELEMENTS

CROSS-REFERENCE TO RELATED APPLICATION

This application is a continuation of U.S. application Ser. No. 13/713,178, filed on Dec. 13, 2012, which application is a divisional of U.S. application Ser. No. 12/770,994, filed on Apr. 30, 2010, the complete disclosures of which are hereby incorporated herein by reference for all purposes.

FIELD OF THE INVENTION

The present invention relates to handheld, personal skin care systems with detachable skin care elements. The skin care elements are coupled to a skin care element holder that fits into a receptacle in a handheld body.

BACKGROUND OF THE INVENTION

Handheld skin care systems having detachable skin care elements are known in the art. The systems generally include a handheld body with a coupling feature to which the detachable skin care element is detachably coupled. The skin care elements are detachably coupled to the handheld body for several reasons including (1) selective attachment of one of several different skin care elements, (2) replacement of disposable skin care elements, and (3) removal for cleaning.

Examples of detachable skin care elements are disclosed in Menke et al., WO 2007/015729A1, in which the detachable skin care elements may be coupled to a handheld body via a cap that fits over a vibrating head. The skin care element may be a disposable pad, such as a sponge, a fibrous material, or other material.

Another example of detachable skin care elements is disclosed in Gubernick et al., EP 2022420. Detachable skin care elements, such as a sponge, a fibrous material, or other material, may be coupled to a handheld body via a carrier that snap-fits into an attachment surface.

The handheld, personal skin care systems having detachable skin care elements described above generally illustrate handheld devices that are motorized to provide vibrating surfaces. It is also desirable to have handheld, personal skin care systems that provide rotating motion.

Therefore, what is needed are detachable skin care elements and skin care element holders that are safe for use with rotating handheld, personal skin care systems, that are easily removable from such systems, and that can also be used with existing handheld bodies for personal skin care.

SUMMARY OF THE INVENTION

Surprisingly, we have found a novel way to address the problem of improved safety in rotating skin care element holders. A skin care element holder is designed for use with a handheld body having a receptacle. The skin care element holder includes a substantially circular plate having a diameter between about 20 and about 60 mm. The substantially circular plate has a first surface arranged and configured for coupling to the skin care element; a second surface, opposite the first surface; and an outer peripheral edge. The second surface of the substantially circular plate has at least one spacer leg; a plurality of engagement arms; and at least one key. Each of the at least one spacer leg, engagement arms and key extend from the second surface in a direction away from the first surface. The at least one spacer leg supports the plate in the receptacle. At least one of said engagement arms includes a snap-fit projection for engagement with a recess in the receptacle. The key is arranged and configured to fit into a notch in the receptacle.

In another aspect of the invention, a skin care system includes a handheld body, a skin care element holder, and a skin care element coupled to the skin care element holder. The handheld body has a generally circular receptacle having a diameter between about 20 and about 60 mm disposed thereon. The generally circular receptacle includes a generally circular floor and a generally circular rim extending away from the handheld body. The floor and rim define a generally cylindrical void volume, and the rim has a notch disposed therein. The skin care element holder includes a substantially circular plate having a diameter corresponding to the diameter of the receptacle. The substantially circular plate has a first surface arranged and configured for coupling to the skin care element, a second surface, opposite the first surface, and an outer peripheral edge. The second surface of the substantially circular plate has at least one spacer leg; a plurality of engagement arms; and at least one key. Each of the at least one spacer leg, engagement arms and key extend from the second surface in a direction away from the first surface. The at least one spacer leg supports the plate in the receptacle. At least one of said engagement arms includes a snap-fit projection for engagement with a recess in the receptacle. The key is arranged and configured to fit into a notch in the receptacle.

In another aspect of the invention, a skin care system includes a handheld body, a skin care element holder, and a skin care element coupled to the skin care element holder. The handheld body having a generally circular receptacle having an inner diameter between about 20 and about 60 mm disposed thereon, and the generally circular receptacle includes a generally circular floor and a rim extending about the generally circular floor and away from the handheld body. The floor and rim define a generally cylindrical void volume, and the rim has at least one recess and a notch disposed therein. The skin care element includes a substantially circular plate having a diameter at least equal to the inner diameter of the receptacle. The substantially circular plate has a first surface arranged and configured for coupling to the skin care element, a second surface, opposite the first surface, and an outer peripheral edge. The second surface of the substantially circular plate has at least one spacer leg extending from the second surface in a direction away from the first surface to support the plate in the receptacle. It also has three engagement arms extending from the second surface proximate the outer peripheral edge in a direction away from the first surface. The three engagement arms are disposed inward from the peripheral edge and located to engage the at least one recess in the rim of the receptacle. At least one of said engagement arms has a snap-fit projection for engagement with a corresponding recess in the rim of the receptacle. The second surface also has at least one key extending from the second surface in a direction away from the first surface that is arranged and configured to fit into the notch in the rim of the receptacle.

BRIEF DESCRIPTION OF THE DRAWING

A more particular description of the invention, briefly summarized above may be had by reference to the embodiments thereof that are illustrated in the appended drawings. It is to be so noted, however, that the appended drawings illustrate only typical embodiments of the invention and, therefore, are not

DETAILED DESCRIPTION OF THE PREFERRED EMBODIMENTS

Figure 1:
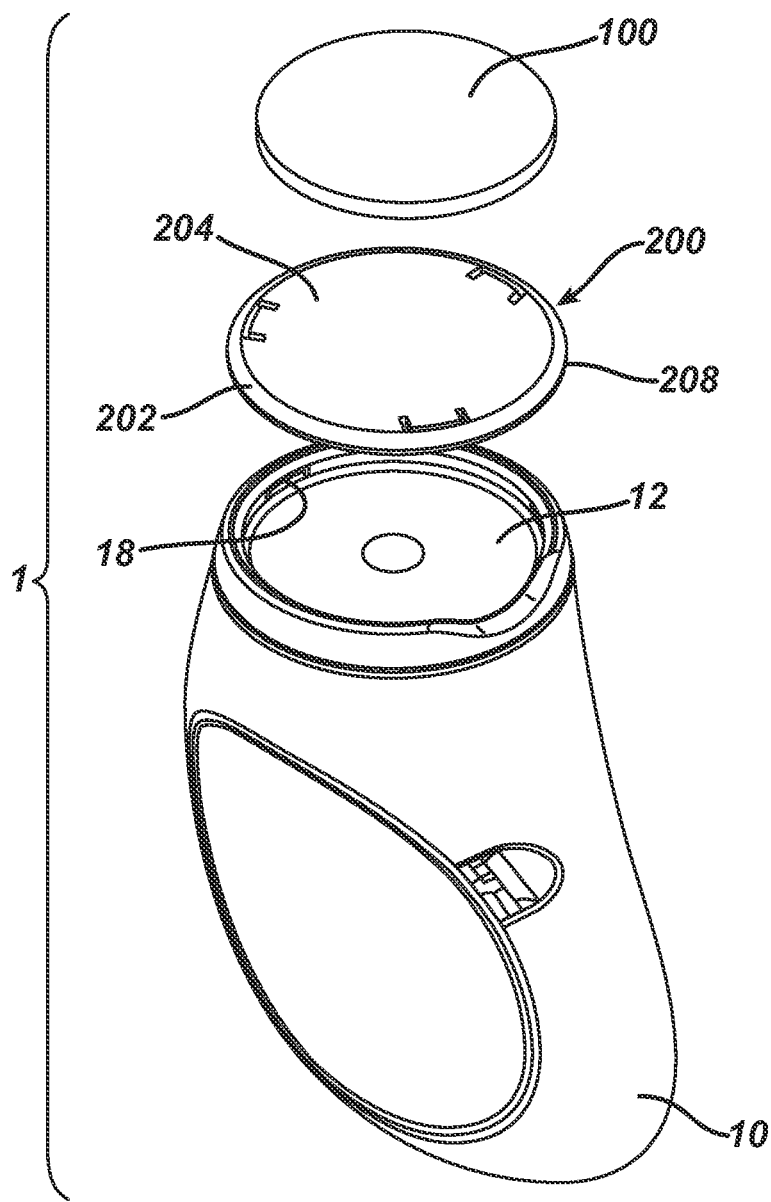
FIG. 1 is a perspective view of a skin care system of the present invention.

It is believed that one skilled in the art can, based upon the description herein, utilize the present invention to its fullest extent. The following specific embodiments are to be construed as merely illustrative and not limiting the remainder of the disclosure in any way whatsoever.

As used herein the specification and the claims, the term "mechanical skin resurfacing technique" and variants thereof relate to the mechanically assisted removal of mammalian (especially human) skin cells, ranging from mild techniques (such as exfoliation and abrasive cleansing) through microdermabrasion, and up to severe techniques such as dermal abrasion.

As used herein the specification and the claims, the term "dermabrasion" and variants thereof relate to a non-thermal resurfacing technique especially well suited for deep defects of the skin such as acne scars, heavy wrinkles and the disfiguring effects of skin conditions like rosacea. The procedure involves the mechanical sanding of the upper layers of the skin and penetrates the skin deeper than microdermabrasion. With dermabrasion, a new layer of skin replaces the abraded skin during healing, resulting in a smoother appearance.

As used herein the specification and the claims, the term "microdermabrasion" and variants thereof relate to a very mild and less-penetrating form of dermabrasion, more suited for reduction of fine lines and wrinkles and for other less severe skin conditions. Microdermabrasion penetrates less deeply into the skin, primarily the stratum corneum, or portions thereof.

As used herein the specification and the claims, the term "exfoliation" and variants thereof relate to the peeling and sloughing off of the skin's tissue cells.

As used herein the specification and the claims, the term "cleansing" and variants thereof relate to removal of dirt, oils, and the like from the surface of the skin, especially through surfactant washing, and perhaps also penetrating into the pores of the skin. In "abrasive cleansing," some degree of exfoliation also occurs.

As used herein the specification and the claims, the term "nonwoven" and variants thereof relate to a sheet, web, or bat of natural and/or man-made fibers or filaments, excluding paper, that have not been converted into yarns, and that are bonded to each other by any of several means. For additional clarification, nonwovens are distinct from woven and knitted fabrics. The fibers included in the nonwoven materials may be staple or continuous or be formed in situ, and preferably, at least about 50% of the fibrous mass is provided by fibers having a length to diameter ratio greater than about 300:1.

The present invention relates to handheld, personal skin care systems with detachable skin care elements. The skin care elements are coupled to a skin care element holder that fits into a receptacle in a handheld body. The skin care elements are especially useful in systems in which the handheld body contains a motor to impart motion to the skin care element, especially spinning and/or oscillating motions.

FIG. 1 depicts one, non-limiting example of a handheld, personal skin care system 1 that includes a handheld body 10 and a skin care element 100 coupled to a skin care element holder 200 that fits into a receptacle 12 in the handheld body 10.

Figure 2:
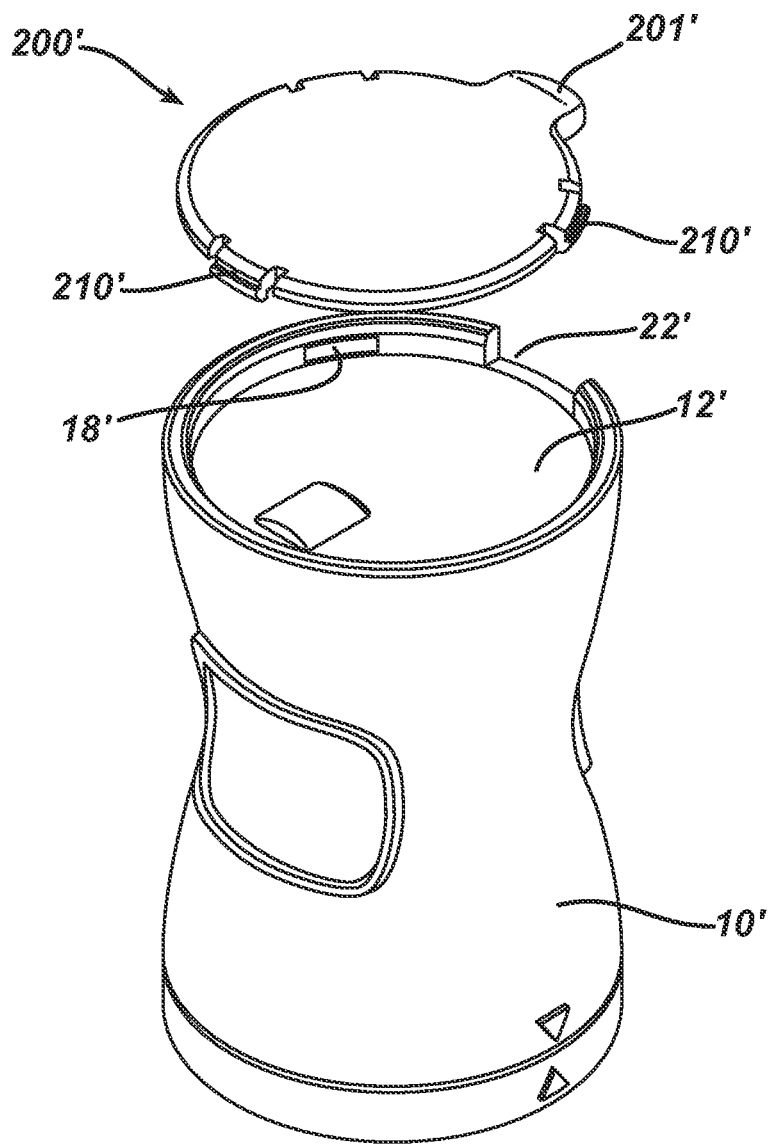
FIG. 2 is a perspective view of a prior art skin care system.

While prior art handheld personal care systems (such as that shown in FIG. 2) sometimes included skin care element holders 200' that fit into a receptacle 12' having three evenly spaced recesses 18' in the handheld body 10', generally, these holders 200' have three evenly spaced engagement arms 210'. In addition, the holders 200' included a tab 201' extending more than 5 mm out from the rest of the holder 200' to aid in its removal from the receptacle 12'. This extension was acceptable in vibratory devices, but we have determined that including these tabs, which provide a hard surface extending radially outward and which may contact sensitive skin, in rotating devices has significant potential to cause injury to a user. However, merely eliminating this tab caused difficulty for removal of the holders from the receptacle. Therefore, we created a new and useful skin care element holder that can be used with spinning and/or oscillating motions and which remains compatible with the previous generation handheld bodies.

Figure 3A:
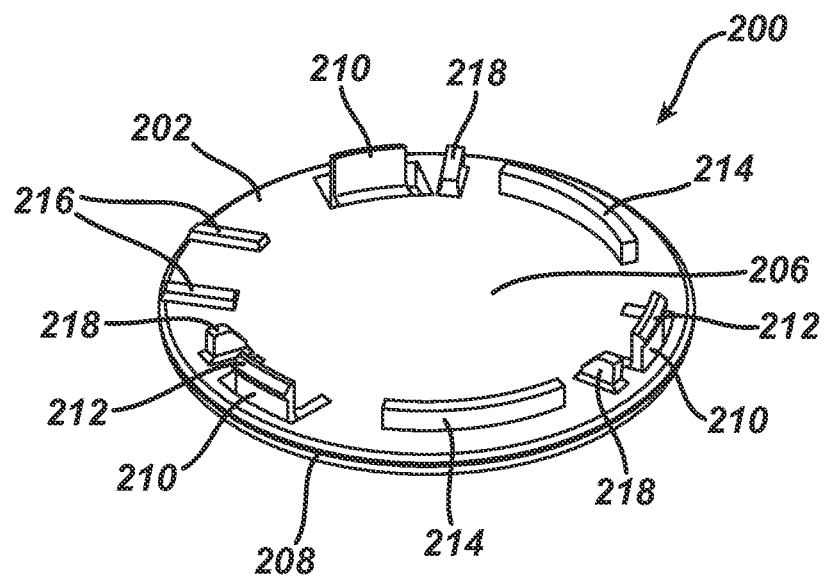
FIG. 3A is a perspective view of the bottom surface of a skincare element holder according to the present invention.

Referring again to FIG. 1, the skin care element holder 200 is a substantially circular plate 202 having a diameter between about 20 mm and about 60 mm. It has a first surface 204 arranged and configured for coupling to the skin care element 100, a second surface 206, opposite the first surface, and an outer peripheral edge 208. The second surface is shown in more detail in FIG. 3. The second surface 206 has a plurality of engagement arms 210 extending from the second surface 206 in a direction away from the first surface, at least one of said engagement arms comprising a snap-fit projection 212 for engagement with recesses in an associated receptacle. At least one spacer leg 214 extends from the second surface 206 in a direction away from the first surface 204 to support the plate 202 when fitted into an associated receptacle. This spacer leg 214 also adds strength to the skin care element holder 200 to help resist damage, especially when the system is mishandled and/or dropped. The plate 202 also has at least one key 216 extending from the second surface 204 in a direction away from the first surface that is arranged and configured to fit into a notch in an associated receptacle. The second surface 206 may also have one or more optional centering flange(s) 218 to improve the fit of the skin care element holder 200 in the receptacle 12. Like the spacer leg(s), this centering flange 218 also adds strength to the skin care element holder 200 to help resist damage. Alternatively, the functions of the spacer leg(s) and the centering flange(s) may be combined into one or more separate structures spaced about the second surface 206.

The engagement arms 210 provide a snap-fit engagement with recesses in an associated receptacle to hold the plate 202 in place during use. Preferably, there are three engagement arms 210, each having a snap-fit projection 212 extending outwardly from the center of the substantially circular plate 202. Alternatively, one or two of the three engagement arms 210 have a flange to fit into a recess associated with a mating receptacle, and the remaining engagement arm(s) have a snap-fit projection. Thus, much like a battery compartment door, one or more flanges fit into a recess in a receptacle, and an opposite engagement arm has a snap fit project to secure the plate in place for use. Preferably, the three engagement arms 210 are substantially evenly spaced around the substantially circular plate 202, such as about 120° around the plate 202. In addition, the engagement arms 210 are disposed proximate, but spaced inward from the outer peripheral edge 208. This permits the second surface 206 of the plate 202 to be positioned above a rim of a receptacle of a handheld body.

Preferably, the at least one spacer leg 214 engages with a surface in an associated receptacle to support the therein. This reduces the likelihood of significant relative motion between the plate 202 and the associated receptacle that may cause an audibly perceptive rattle during use. In addition, the at least one key 216 extending from the second surface 204 of the plate 202 can engage a notch in an associated receptacle. This key 216 can cooperate with the engagement arms 210 to prevent significant relative rotational motion between the plate 202 and receptacle 12 during use.

Figure 3B:
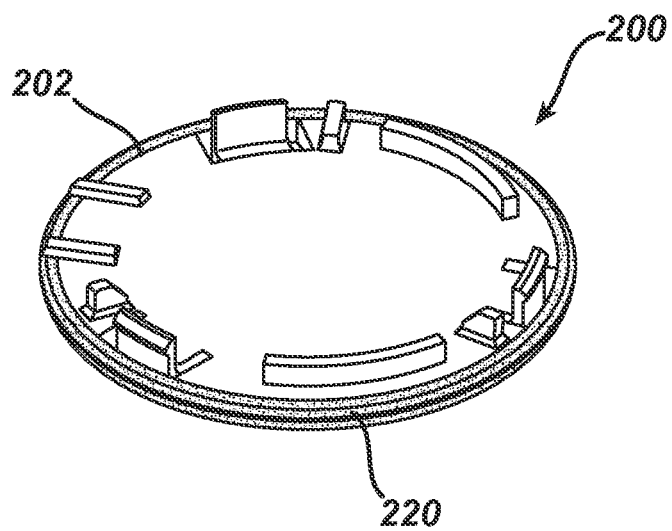
FIG. 3B is a perspective view of the bottom surface of an alternative skincare element holder according to the present invention.

Preferably, the outer peripheral edge 208 of the substantially circular plate 202 is the outer circumference of a circle of constant radius from the center of the plate. In this embodiment, the plate 202 is truly circular. Alternatively, the outer peripheral edge 208 is defined by a geometrical surface having a variable radius from the center of the plate; however, the maximum radius and minimum radius have a difference of less than about 3 mm, and more preferably of less than about 2 mm. This generally circular form of the plate improves the safety of the system for a rotating or oscillating skin care system. In yet another alternative form, the outer peripheral edge 208 may have a resilient material 220 (as shown in FIG. 3B) disposed thereon to cushion any irregularities in the peripheral edge 208.

Figure 4A:
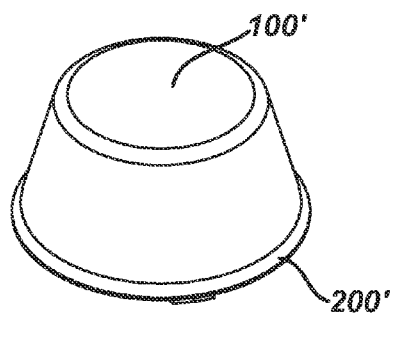
FIG. 4A-4D are perspective views of various skin care elements coupled to respective skin care element holders according to the present invention.
Figure 4B:
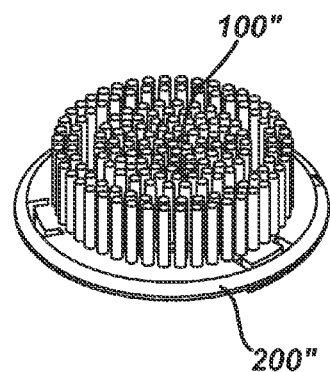
Figure 4C:
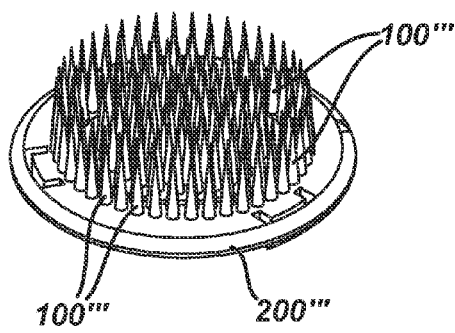

The skin care element 100 is coupled to the skin care element holder 200. This coupling may be permanent or releasable, but in either event, it is preferred that the coupling be water-resistant. Permanent attachment can be adhesive, mechanical, chemical, and the like. Permanently attached skin care elements include without limitation working elements such as massage elements and abrasive elements including abrasive materials such as stones, injection molded textured surfaces, molded surfaces with bonded abrasive particles (including molded surfaces with abrasive particles dusted on the surface while it is still molten), and the like; carrier elements such as sponges, brushes, molded fingers, molded cups, and the like. These permanently attached skin care elements can also provide more than one feature or use, such as abrasive and carrier or massage and carrier. One example of a permanently attached skin care element 100' is shown in FIG. 4A. In this embodiment, an abrasive stone 100' is permanently attached to a skin care element holder 200'. In FIG. 4B, a brush 100" is permanently attached to a skin care element holder 200". In FIG. 4C, a molded fingers 100'" are permanently attached to a skin care element holder 200'.

As used herein the specification and the claims, the term "brush" and variants thereof relate to a device having bristles (short, stiff, coarse materials such as hair, filaments, strands, wires, fibers, and the like) that are set into and extend from a substrate, such as a backing or handle.

Figure 4D:
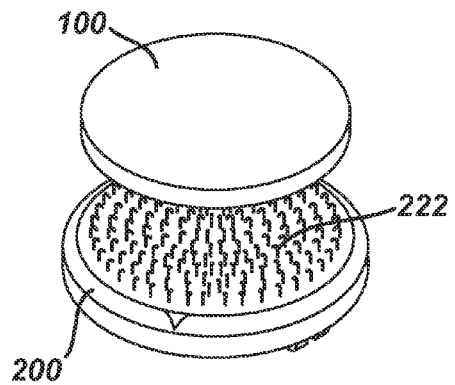

Releasable attachment can also be adhesive, mechanical, chemical, and the like. Preferably, the releasable attachment is mechanical, such as through a hook-and-loop fastener system 222 (shown in FIG. 4D) such as disclosed in Menke et al., WO 2007/015729A1, the contents of which are herein incorporated by reference. Releasably attached skin care elements include without limitation, carrier elements such as sponges, brushes, fibrous pads, and the like; working elements such as massage elements and abrasive elements and the like. Abrasive materials may include abrasive pads, emery cloth, and the like.

Figure 5:
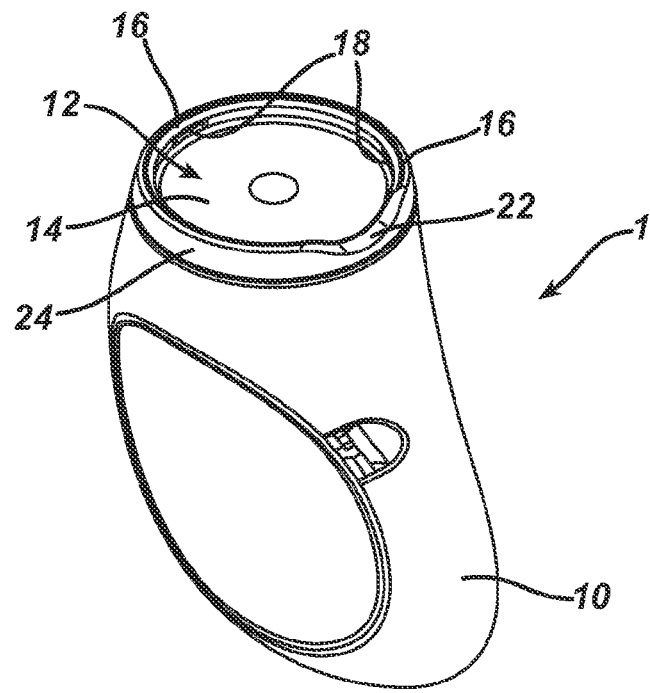
FIG. 5 is an enlarged view of the handheld body of FIG. 1.

Referring now to FIG. 5, the handheld body 10 includes a generally circular receptacle 12 for the skin care element holder. The receptacle 12 includes a generally circular floor 14 and a rim 16 extending about the generally circular floor 14. The rim extends away from the handheld body 10, and the floor and rim define a generally cylindrical volume for accepting the skin care element holder 200. The rim 16 has at least one recess 18 for accepting the engagement arms 210 of the skin care element holder 200. Preferably, the rim 16 has three separate recesses 18 relatively equally spaced about its inner wall 20. These three, equally spaced recesses 18 can then accommodate the three, equally spaced engagement arms 210 of the skin care element holder 200. In addition, the rim 16 includes a notch 22 arranged and configured to accept the key 216 of the skin care element holder 200. The interaction between the notch 22 and key 216 helps to prevent relative rotational movement between the receptacle 12 and the skin care element holder 200. The notch 22 also provides finger lift access for a user to urge or otherwise pry the skin care element holder 200 out of the receptacle 12. In the embodiment of FIG. 5, the receptacle 12 is part of a moveable element 24 that is operatively connected to a motor 26 located within the handheld body 10. This moveable element 24 can be moved by the motor in various desired motions including vibrating, rotating (about an axis of rotation), oscillating (about an axis of rotation), reciprocating (generally along a line), orbiting (moving as a unit about an axis of rotation while maintaining an orientation), and the like, as well as combinations of one or more of these motions.

Figure 6:
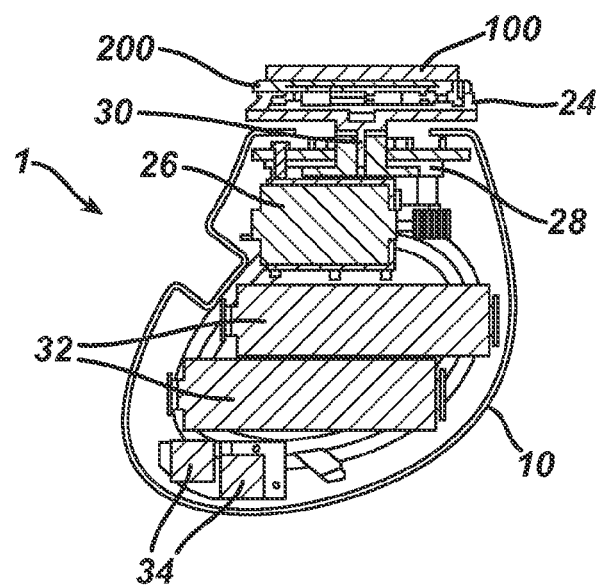
FIG. 6 is a view of the interior of the handheld body of FIG. 5.

As shown in FIG. 6, a preferred embodiment of the handheld body 10 includes a motor 26, a transmission 28, and a drive shaft 30 that is operatively connected to the moveable element 24. The handheld body 10 of this embodiment also includes one or more batteries 32 to power the system. This embodiment also includes one or more electrical switches 34 that control the motor 26 and the motion of the moveable element 24. These switches may include a power switch, speed selector, motion type and direction, and other desired functions.

Preferably, the handheld body 10 is water-resistant to permit its safe use in the bathroom and/or shower. Therefore, any moving shafts and/or switches that penetrate the body would be appropriately sealed, and the shell components that form the body would also be appropriately sealed to prevent water from entering the interior of the handheld body.

Skin care system 1 of the present invention may be used for skin care, including skin treatments such as mechanical skin resurfacing (including microdermabrasion), acne treatment, and the like; and skin care routines such as cleansing, mild exfoliation, massaging, anti-aging, firmness, toning and texturing, hair removal, body shaping, cellulite removal, and the like.

In one embodiment of the invention, the skin care element holder 200 is inserted into the receptacle 12 on the handheld body 10, and the skin care element 100 is coupled thereto (see, for example, FIG. 6).

The motor is then powered, and the skin care element 100 is moved across the face or other expanse of skin to be treated. The skin care element 100 may have incorporated therewith a formulation to provide emoliency, foam, or delivery of benefit agents to the skin. When the user is finished, the skin care element 100 may be removed and later replaced with a fresh one to provide a hygienic surface.

The skin care system 1 may be used with an additional composition (e.g., a cream or paste) to provide lubrication, deliver actives, or provide an overall aesthetic experience. The composition may be free of abrasives (pumice, oxides. etc.) that would otherwise potentially embed in the skin. Alternatively, the composition may include abrasives, however, in this embodiment, the user would preferably rinse the abrasive composition from the skin after the treatment is complete. The composition may be placed by the user (e.g., by dipping the skin-contactable element into the cream) on the skin-contactable element prior to empowering the apparatus. Furthermore, the skin care element 100 may deliver of benefit agents, lubrication, and lathering. Thus, it is often desirable to have a pad or other skin care element dosed with a skin care composition, such as a moisturizer, toner, cleanser, and the like.

The elements of the skin care system may be manufactured and assembled by any useful means that will be recognized by one of ordinary skill in the art. The skin care element may be made as appropriate, depending upon the actual element desired. Methods of making useful skin care elements are disclosed in US Menke et al., WO 2007/015729A1, Gubernick et al., EP 2022420, Batchvarova et al., U.S. Ser. No. 12/764,479, filed Apr. 21, 2010 (published as US-2011-0258791-A1 and issued as U.S. Pat. No. 8,308,702), the contents of which are herein incorporated by reference. The skin care element holder may be manufactured by any useful means that will be recognized by one of ordinary skill in the art. Preferably, the skin care element holder is formed via injection molding.

The specification, embodiments, and examples above are presented to aid in the complete and non-limiting understanding of the invention disclosed herein. Since many variations and embodiments of the invention can be made without departing from its spirit and scope, the invention resides in the claims hereinafter appended.

What is claimed is:

1. A skin care element holder for use with a handheld body having a receptacle, said skin care element holder comprising a substantially circular plate having a diameter between about 20 and about 60 mm, wherein:
   a. said substantially circular plate has:
      i. a first surface arranged and configured for coupling to the skin care element;
      ii. a second surface, opposite said first surface; and
      iii. an outer peripheral edge; and
   b. said second surface of said substantially circular plate has:
      i. at least one spacer leg extending from said second surface in a direction away from said first surface to support said plate in the receptacle;
      ii. at least one engagement arm extending from said second surface at a location spaced radially inwardly of said outer peripheral edge of said plate and radially offset from spacer leg, and in a direction away from said first surface, said at least one engagement arm comprising a snap-fit projection for engagement with a recess in the receptacle;
      iii. at least one key extending from said second surface, in a direction away from said first surface, at least from a location radially outward of said location from which said at least one spacer leg extends and said location from which said at least one engagement arm extends up to a location at, but not beyond, said outer peripheral edge of said plate, said at least one key being arranged and configured to fit into a notch in the receptacle.

2. The skin care element holder of claim 1, wherein:
said key has an engagement surface along a free end of said at least one raised portion furthest from said second surface, said engagement surface being configured to engage the notch in the receptacle of the handheld body; and
said snap-fit projection engages in the recess in the receptacle of the handheld body in a radial direction.

* * * * *